(12) United States Patent
Atehortua et al.

(10) Patent No.: US 7,521,238 B2
(45) Date of Patent: Apr. 21, 2009

(54) **TISSUE CULTURE MEDIUM FOR *MACADAMIA* AND *THEOBROMA CACAO***

(75) Inventors: Lucia Atehortua, Medellin (CO); Esther Julia Naranjo, Medellin (CO); Andrea Lorena Herrera, Medellin (CO); Adriana Maria Gallego, Medellin (CO)

(73) Assignee: Universidad De Antioquia, Medellin (CO)

( * ) Notice: Subject to any disclaimer, the term of this patent is extended or adjusted under 35 U.S.C. 154(b) by 142 days.

(21) Appl. No.: 11/613,865

(22) Filed: Dec. 20, 2006

(65) Prior Publication Data

US 2008/0153165 A1    Jun. 26, 2008

(51) Int. Cl.
*C12N 5/00*    (2006.01)
*C12N 5/02*    (2006.01)

(52) U.S. Cl. ........................................ 435/431; 435/420
(58) Field of Classification Search ....................... None
See application file for complete search history.

*Primary Examiner*—Wendy C. Haas
(74) *Attorney, Agent, or Firm*—Martinez Patents P.C.; John J. Martinez

(57) ABSTRACT

The present invention provides a method and a culture medium for the production of food biomass by directly culturing seed kernel tissue, or seed cotyledonary differentiated tissue. The culture medium of the present invention contains at least DKW culture medium, Vitamin MS culture medium with an enriched concentration of thiamine, sacarose, kinetine, adenine, 2,4diclorofenoxiacético (2,4D), L-Glutamine, cysteine, ascorbic acid, and Gelrite®.

7 Claims, 1 Drawing Sheet

TISSUE CULTURE MEDIUM FOR *MACADAMIA* AND *THEOBROMA CACAO*

FIELD OF THE INVENTION

The invention is related to a method and a culture medium for the production of food biomass from plant seed differentiated tissue.

BACKGROUND OF THE INVENTION

The U.S. Pat. No. 4,204,366 by Janick, Jules et al. describes a method for the production of cotyledons by non-agricultural means. However, the method described by Janick requires propagating or culturing asexual embryos. Regeneration of plants by somatic embryogenesis has also been described by Sondahl, M. R. et al (U.S. Pat. No. 5,312,801)

The present invention provides a culture medium and a method to produce food biomass by directly culturing seed differentiated and mature tissue without propagating or culturing embryos.

SUMMARY OF THE INVENTION

The invention of the present application provides a non-agricultural method good for vegetal food production, wherein the method does not require growing cacao plants, clonal propagation of plants by embryogenesis, or production of cotyledons by embryogenesis. In addition, the method of the present invention can be scaled up in a laboratory or bioreactor without worrying about weather conditions or contamination by virus or plagues. This new non-agricultural method for vegetal food biomass production is a new answer to the increasing need of food for the world population The object of the present invention is to provide a method and a culture medium for the production of biomass by directly culturing seed kernel, or seed cotyledonary differentiated tissue.

The culture medium of the present invention contains at least DKW culture medium, Vitamin MS culture medium with an enriched concentration of thiamine, sacarose, kinetin, adenine, 2,4-Dichlorophenoxyacetic acid (2,4D), L-Glutamine, cysteine, ascorbic acid, and GELRITE.

Specifically, the present invention provides a method and culture media for the production of biomass from seed cotyledonary differentiated tissue or seed kernel from plants from the Sterculiacea and Proteaceae families respectively.

Objectives and additional advantages of the present invention will become more evident in the description of the figures, the detailed description of the invention and the claims.

DETAILED DESCRIPTION OF THE INVENTION

Figure 1:
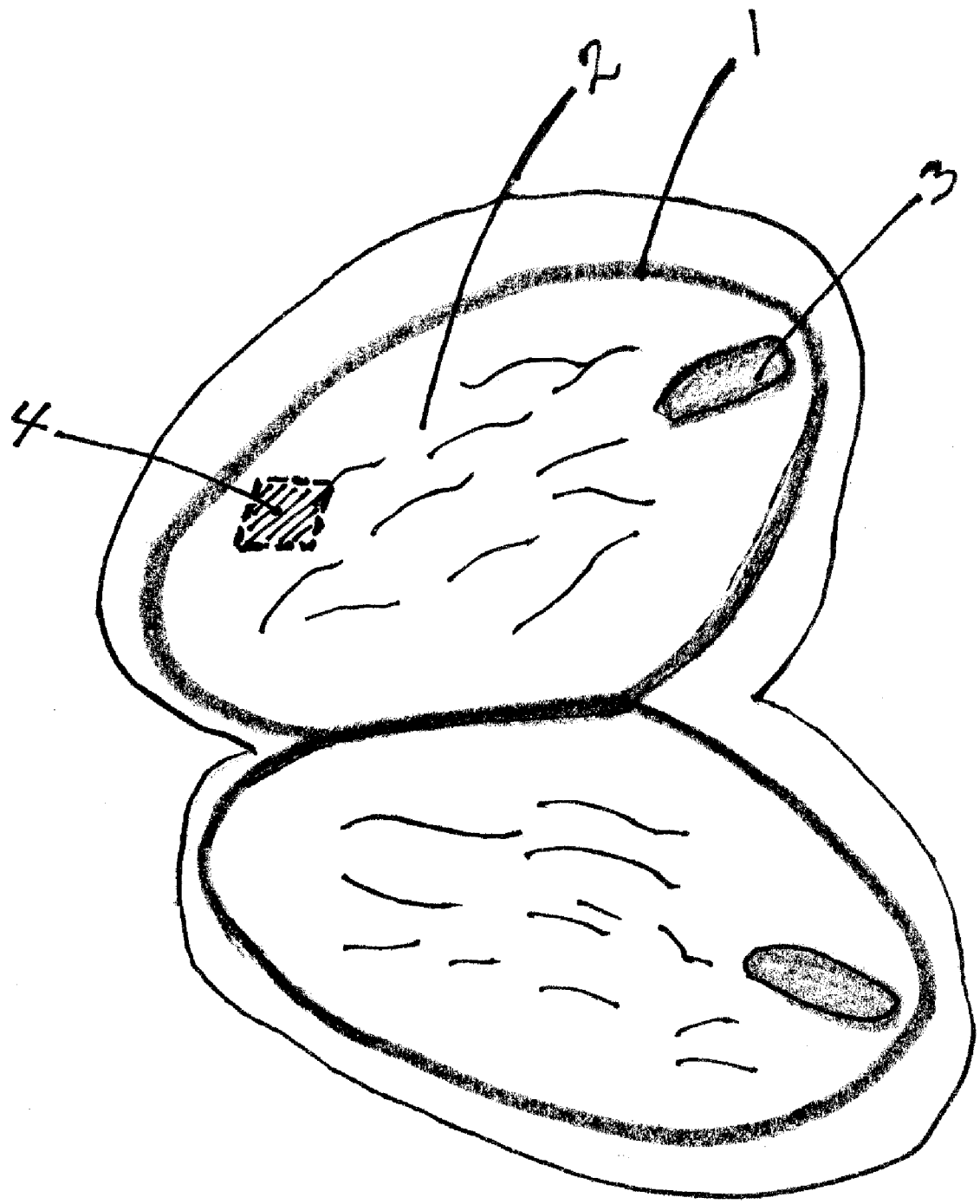
FIG. 1 is an illustration of a *Theobroma cacao* (Sterculiacea family) plant seed and a representation of the portion where the sample of cotyledonary differentiated tissue is taken from, to culture for the production of cacao biomass.

The object of the present invention is to provide a culture medium for the production of biomass from plant seed differentiated and mature tissue comprising at least DKW culture medium, Vitamin MS culture medium with an enriched concentration of thiamine, sacarose in a concentration between 15 and 40 g/L, kinetin in a concentration between 0.5 and 4 mg/L, adenine in a concentration between 0.2 and 5 mg/L, 2,4-Dichlorophenoxyacetic acid (2,4D) in a concentration between 1 and 5 mg/L, L-Glutamine in a concentration between 20 and 100 mg/L, cysteine in a concentration between 10 and 100 mg/L, ascorbic acid in a concentration between 20 and 110 mg/L, and GELRITE in a concentration between 0.7 and 2.0 g/L, wherein the culture medium has the pH adjusted between 5.5 and 6.0.

In a prefer embodiment, the culture medium of the present invention comprises at least agar, DKW culture medium, Vitamin MS (Murashige and Skoog) culture medium with an enriched concentration of thiamine, sacarose in a concentration of 20 g/L, kinetin in a concentration of 2 mg/L, adenine in a concentration of 1 mg/L, 2,4-Dichlorophenoxyacetic acid (2,4D) in a concentration of 4 mg/L, L-Glutamine in a concentration of 50 mg/L, cysteine in a concentration of 20 mg/L, ascorbic acid in a concentration of 20 mg/L, and GELRITE in a concentration of 1.6 g/L, wherein the culture medium has the pH adjusted to 5.8, and wherein the DKW culture medium and the Vitamin MS culture medium concentrations per liter are prepared according to the suggested standard commercial guidelines.

FIG. 1 is an illustration of the parts of a *Theobroma cacao* seed: seed coat (1); cotyledonary differentiated tissue (2); and embryo (3).

FIG. 1 also shows a representation of one aspect of the present invention where a portion sample of seed differentiated and mature tissue (4)(shaded area) is cotyledonary differentiated tissue (3). In this aspect of the invention the seed differentiated and mature tissue is from a plant from the Sterculiacea family. In a preferred embodiment of this aspect of the present invention, the plant from the Sterculiacea family is from the *Theobroma* genus. Yet, in a more preferred embodiment of this aspect of the present invention the plant from the Sterculiacea plant is from the *T. cacao* species.

In another aspect of the present invention, the plant seed differentiated and mature tissue is seed kernel, wherein the plant seed differentiated tissue is from a plant from the Proteaceae family. In a preferred embodiment of this another aspect of the present invention, the plant from the Proteaceae family is from the *Macadamia* genus. Yet, in a more preferred embodiment of this another aspect of the present invention, the plant from the Proteaceae family is from the *Macadamia* species.

In addition, the second object of the present invention is to provide a method for the production of biomass from Sterculiacea plant differentiated and mature tissue comprising:
  A. Obtaining a fruit that is between three and five months old;
  B. Cleaning and sterilizing said fruit;
  C. Extracting seeds from said fruit;
  D. Discarding the embryo and obtaining a sample of cotyledonary differentiated tissue;
  E. Putting the sample of cotyledonary differentiated tissue in contact with culture medium;
  F. Incubating under light with a determined wave length, and at a temperature between 15 and 35° C., until biomass is produced; and,
  G. Collecting grown biomass tissue by retiring said grown biomass tissue from the culture medium.

Wherein in one aspect of the method of the present invention the culture medium contains at least DKW culture medium, Vitamin MS culture medium with an enriched concentration of thiamine, sacarose in a concentration between 15 and 40 g/L, kinetin in a concentration between 0.5 and 4 mg/L, adenine in a concentration between 0.2 and 5 mg/L, 2,4-Dichlorophenoxyacetic acid (2,4D) in a concentration between 1 and 5 mg/L, L-Glutamine in a concentration between 20 and 100 mg/L, cysteine in a concentration between 10 and 100 mg/L, ascorbic acid in a concentration between 20 and 110 mg/L, and GELRITE in a concentration between 0.7 and 2.0 g/L; and wherein the pH of said culture medium is adjusted to a range between 5.5 and 6.0. However, in a preferred embodiment of this aspect of the method of the present invention, the culture medium contains at least agar, DKW culture medium, Vitamin MS (Murashige and Skoog) culture medium with an enriched concentration of thiamine, sacarose in a concentration of 20 g/L, kinetin in a concentration of 2 mg/L, adenine in a concentration of 1 mg/L, 2,4-Dichlorophenoxyacetic acid (2,4D) in a concentration of 4 mg/L, L-Glutamine in a concentration of 50 mg/L, cysteine in a concentration of 20 mg/L, ascorbic acid in a concentration of 20 mg/L, and GELRITE in a concentration of 1.6 g/L; and the pH of the culture medium is adjusted to 5.8.

In one more aspect of the method of the present invention, the cotyledonary differentiated and mature tissue is from a Sterculiacea plant from the *Theobroma* genus. Still, in a preferred embodiment of this aspect of the present invention the Sterculiacea plant is from the *T. cacao* species.

In a preferred embodiment of another additional aspect of the method of the present invention the sample of cotyledonary differentiated and mature tissue in contact with the culture medium is incubated under total darkness.

Moreover, the third object of the present invention is to provide a method for the production of biomass from Proteaceae plant differentiated and mature tissue comprising:
  a. Obtaining a sample of kernel differentiated tissue;
  b. Putting the sample of kernel differentiated tissue in contact with culture medium;
  c. Incubating under light with a determined wave length, and at a temperature between 15 and 35° C., until biomass is produced; and,
  d. Collecting grown biomass by retiring said grown biomass from the culture medium.

Wherein in one aspect of the method for the production of biomass from Proteaceae plant differentiated and mature tissue, the culture medium contains at least DKW culture medium, Vitamin MS culture medium with an enriched concentration of thiamine, sacarose in a concentration between 15 and 40 g/L, kinetin in a concentration between 0.5 and 4 mg/L, adenine in a concentration between 0.2 and 5 mg/L, 2,4-Dichlorophenoxyacetic acid (2,4D) in a concentration between 1 and 5 mg/L, L-Glutamine in a concentration between 20 and 100 mg/L, cysteine in a concentration between 10 and 100 mg/L, ascorbic acid in a concentration between 20 and 110 mg/L, and GELRITE in a concentration between 0.7 and 2.0 g/L; and wherein the pH of said culture medium is adjusted to a range between 5.5 and 6.0. However, in a preferred embodiment of this aspect of the method of the present invention, the culture medium contains at least agar, DKW culture medium, Vitamin MS (Murashige and Skoog) culture medium with an enriched concentration of thiamine, sacarose in a concentration of 20 g/L, kinetin in a concentration of 2 mg/L, adenine in a concentration of 1 mg/L, 2,4-Dichlorophenoxyacetic acid (2,4D) in a concentration of 4 mg/L, L-Glutamine in a concentration of 50 mg/L, cysteine in a concentration of 20 mg/L, ascorbic acid in a concentration of 20 mg/L, and GELRITE in a concentration of 1.6 g/L; and the pH of the culture medium is adjusted to 5.8.

In one more aspect of the method for the production of biomass from Proteaceae plant differentiated and mature tissue, the seed kernel differentiated tissue is from a Proteaceae plant from the *Macadamia* genus. Still in a preferred embodiment of this aspect of this method, the Proteaceae plant is from the *Macadamia* species.

In a preferred embodiment of another additional aspect of the method for the production of biomass from Proteaceae plant differentiated and mature tissue, the sample of kernel differentiated tissue in contact with the culture medium is incubated under total darkness.

The method and culture of the present invention could also be applied for the production of biomass from seed differentiated tissue from other nut plants, as for example; almonds, walnuts, cashew nuts, Brazil nuts, hazelnuts, chestnuts, chickpeas, pistachios, pecan nuts, pine nuts, peanuts, heart nuts, persina walnuts, etc.

While the description presents the preferred embodiments of the present invention, additional changes can be made in the form and disposition of the parts without distancing from the basic ideas and principles comprised in the claims.

EXAMPLE

Materials and Methods

The culture medium for production of biomass was prepared as follows:

Agar, DKW culture medium, Vitamin MS (Murashige and Skoog) culture medium with an enriched concentration of thiamine, sacarose 20 g/L, kinetin 2 mg/L, adenine 1 mg/L, 2,4-Dichlorophenoxyacetic acid (2,4D) 4 mg/L, L-Glutamine 50 mg/L, cysteine 20 mg/L, ascorbic acid 20 mg/L, and GELRITE 1.6 g/L. The culture medium has the pH adjusted to 5.8, and the DKW culture medium and the Vitamin MS culture medium concentrations were prepared according to the suggested standard commercial guidelines.

Three to four month old cacao fruits were obtained from a Colombian farm. The cacao fruits were cleaned and sterilized. The seed from said fruits were extracted. The embryos from the cacao seed were discarded. Samples of approximately 5 mm from the cotyledonary differentiated tissue were cut from the seed. The cotyledonary differentiated tissue samples were put in Petri plates with the culture medium. The culture plates with the cotyledonary differentiated tissue samples were incubated under darkness at room temperature for 1-3 months. The new grown dark brown biomass tissue buds were collected by separating it from the solid culture medium. The dark brown tissue buds were split into several pieces and each was re-inoculated into a new Petri plate with the culture medium. After approximately one month, the new dark brown tissue buds were collected again.

The collected dark brown tissue buds have a cacao flavor when orally tasted. In addition, preliminary analysis of the dark brown tissue buds shows that they contain at least cacao butter and cacao carbohydrates.

Fresh mature macadamia fruits were obtained in a local market. The macadamia fruits were cleaned and sterilized. Inside a flow chamber, samples of approximately 5 mm from the kernel differentiated and mature tissue of the fruit were cut. The kernel differentiated and mature tissue samples were put in Petri plates with the culture medium. The culture plates with the kernel differentiated and mature tissue samples were incubated under darkness at room temperature for 1-3 months. The new grown whitish creamy biomass tissue buds were collected by separating it from the solid culture medium. The whitish creamy biomass tissue buds were split into several pieces and each piece was re-inoculated into a new Petri plate with culture medium. After approximately one month, the new whitish creamy biomass tissue buds were collected again.

The collected whitish creamy biomass tissue buds from macadamia beans was macroscopically analyzed with a light microscope, in which, fatty tissue was observed. This initial observation suggests that said biomass contains at least macadamia fat components. In addition, the whitish creamy biomass tissue buds have macadamia flavor when orally tested.

The invention claimed is:

1. A culture medium for the production of biomass from plant seed differentiated tissue comprising at least DKW culture medium, Vitamin MS culture medium with an enriched concentration of thiamine, sacarose in a concentration between 15 and 40 g/L, kinetin in a concentration between 0.5 and 4 mg/L, adenine in a concentration between 0.2 and 5 mg/L, 2,4-Dichlorophenoxyacetic acid (2,4D) in a concentration between 1 and 5 mg/L, L-Glutamine in a concentration between 20 and 100 mg/L, cysteine in a concentration between 10 and 100 mg/L, ascorbic acid in a concentration between 20 and 110 mg/L, and GELRITE in a concentration between 0.7 and 2.0 g/L, wherein the culture medium has the pH adjusted between 5.5 and 6.0.

2. The culture medium of claim 1, wherein the plant seed differentiated tissue is cotyledonary differentiated tissue, and wherein the plant seed differentiated tissue is from a plant from the Sterculiacea family.

3. The culture medium of claim 2, wherein the plant from the Sterculiacea family is from the *Theobroma* genus.

4. The culture medium of claim 2, wherein the plant from the Sterculiacea plant is from the *T. cacao* species.

5. The culture medium of claim 1, wherein the plant seed differentiated tissue is seed kernel, and wherein the plant seed differentiated tissue is from a plant from the Proteaceae family.

6. The culture medium of claim 5, wherein the plant from the Proteaceae family is from the *Macadamia* genus.

7. The culture medium of claim 5, wherein the plant from the Proteaceae family is from the *Macadamia* species.

* * * * *